United States Patent [19]

Faull

[11] Patent Number: 6,022,869

[45] Date of Patent: Feb. 8, 2000

[54] AMINOHETEROCYCLIC COMPOUNDS WITH ANTITHROMBOTIC/ ANTICOAGULANT EFFECT

[75] Inventor: Alan Wellington Faull, Macclesfield, United Kingdom

[73] Assignee: Zeneca Limited, London, United Kingdom

[21] Appl. No.: 09/117,673

[22] PCT Filed: Jan. 31, 1997

[86] PCT No.: PCT/GB97/00270

§ 371 Date: Aug. 4, 1998

§ 102(e) Date: Aug. 4, 1998

[87] PCT Pub. No.: WO97/29104

PCT Pub. Date: Aug. 14, 1997

[30] Foreign Application Priority Data

Feb. 5, 1996 [GB] United Kingdom ............... 9602294

[51] Int. Cl.$^7$ .................. A61K 31/495; C07D 295/04
[52] U.S. Cl. ............. 514/227.8; 514/252; 544/60; 544/364
[58] Field of Search ............ 544/364, 60; 514/252, 514/227.8

[56] References Cited

U.S. PATENT DOCUMENTS

| 4,537,896 | 8/1985 | Claeson et al. .................. 544/364 |

FOREIGN PATENT DOCUMENTS

| 0 097 630 | 1/1984 | European Pat. Off. .............. 544/364 |
| 0 097 630 A2 | 1/1984 | European Pat. Off. . |
| 0 232 740 | 8/1987 | European Pat. Off. ............ 548/304.7 |
| 0 232 740 A1 | 8/1987 | European Pat. Off. . |
| 0 555 824 | 8/1993 | European Pat. Off. ............ 548/304.7 |
| 0 555 824 A1 | 8/1993 | European Pat. Off. . |
| 0 608 759 | 8/1994 | European Pat. Off. ............... 544/364 |
| 0 608 759 A2 | 8/1994 | European Pat. Off. . |
| 92/08709 | 5/1992 | WIPO ....................................... 54/364 |
| WO 92/08709 | 5/1992 | WIPO . |
| 94/18185 | 8/1994 | WIPO ................................... 544/364 |
| WO 94/18185 | 8/1994 | WIPO . |
| 96/05189 | 2/1996 | WIPO ................................... 544/364 |
| WO 96/05189 | 2/1996 | WIPO . |
| 96/10022 | 4/1996 | WIPO ................................... 544/364 |
| WO 96/10022 | 4/1996 | WIPO . |
| 97/06802 | 2/1997 | WIPO ................................... 544/364 |
| WO 97/06802 | 2/1997 | WIPO . |

OTHER PUBLICATIONS

R.B. Wallis, "Inhibitors of Coagulation Factor Xa: From Macromolecular Beginnings to Small Molecules", Current Opinion in Therapeutic Patents, 1173–1179 (1993).

J.R. Smith et al., "Fibrin, Red Cell and Platelet Interactions in an Experimental Model of Thrombosis", Br. J. Pharmac., 77:029–038 (1982).

G. Vogel et al., "Comparison of Two Experimental Thrombosis Models in Rats Effects of Four Glycosaminoglycans", Thromb. Res., 54:399–410 (1989).

C. Kettner et al., "The Selective Inhibition of Thrombin by Peptides of Boroarginine", J. Biol. Chem., 265 (30) :18289–18297 (1990).

E. Jucker, "Über C–substituierte Piperazinderivate", Helv. Chim. Acta, 45:2383–2042 (1962).

*Primary Examiner*—Joseph K. McKane
*Attorney, Agent, or Firm*—Finnegan, Henderson, Farabow, Garrett & Dunner, L.L.P.

[57] ABSTRACT

The invention relates to compounds of formula (I), and pharmaceutically-acceptable salts thereof, which possess antithrombotic and anticoagulant properties; processes for preparing compounds of formula (I) and pharmaceutical compositions.

9 Claims, No Drawings

AMINOHETEROCYCLIC COMPOUNDS WITH ANTITHROMBOTIC/ANTICOAGULANT EFFECT

The invention relates to a group of aminoheterocyclic derivatives, and pharmaceutically-acceptable salts thereof, which possess antithrombotic and anticoagulant properties and are accordingly useful in methods of treatment of the human or animal body. The invention also relates to processes for the preparation of said aminoheterocyclic derivatives, to pharmaceutical compositions containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by R. B. Wallis, *Current Opinion in Therapeutic Patents*, 1993, 1173–1179. Thus it is known that two proteins, one known as antistasin and the other known as tick anticoagulant protein (TAP), are specific Factor Xa inhibitors which possess antithrombotic properties in various animal models of thrombotic disease.

It is also known that certain non-peptidic compounds possess Factor Xa inhibitory properties. Of the low molecular weight inhibitors mentioned in the review by R. B. Wallis, all possessed a strongly basic group such as an amidinophenyl or amidinonaphthyl group.

It is the object of the present invention to provide a new class of agent which lacks the amidino group previously believed to be an essential feature for a Factor Xa inhibitor.

We have now found that certain amino-substituted heterocyclic derivatives possess Factor Xa inhibitory activity and in particular also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

The compounds of the present invention possess activity in the treatment or prevention of a variety of medical disorders where anticoagulant therapy is indicated, for example in the treatment or prevention of thrombotic events associated with coronary artery and cerebro-vascular disease. Further examples of such medical disorders include various cardiovascular and cerebrovascular conditions such as myocardial infarction, the formation of atherosclerotic plaques, venous or arterial thrombosis, coagulation syndromes, disseminated intravascular coagulation, vascular injury including reocclusion and restenosis following angioplasty and coronary artery bypass surgery, thrombus formation after the application of blood vessel operative techniques or after general surgery such as hip replacement surgery, the introduction of artificial heart valves or on the recirculation of blood, cerebral infarction, cerebral thrombosis, stroke, cerebral embolism, pulmonary embolism, ischaemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

According to one aspect of the invention there is provided an aminoheterocyclic derivative of formula I,

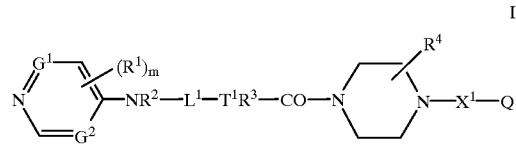

wherein $G^1$ and $G^2$ independently represent CH or N;

m is 0, 1 or 2;

$R^1$ is halogeno, trifluoromethyl, trifluoromethoxy, cyano, $NR^5R^6$, hydroxy, nitro, (1–4C)alkyl or (1–4C)alkoxy;

$T^1$ is CH or N;

$L^1$ is (1–4C)alkylene, (3–6C)cycloalkane-1,2-diyl or (1–3C)alkylene-carbonyl;

$R^2$ is hydrogen or (1–4C)alkyl and $R^3$ is hydrogen or (1–4C)alkyl, or $R^2$ and $R^3$ together form a (1–4C) alkylene or methylenecarbonyl group, wherein 1 or 2 methylene groups within $L^1$ or the ring formed when $R^2$ and $R^3$ are linked optionally bears 1 or 2 substituents selected from carboxy, $CONR^5R^6$, (1–4C)alkyl, (1–4C)alkoxycarbonyl, pyrrolidin-1-ylcarbonyl, piperidinocarbonyl, morpholinocarbonyl, piperazin-1-ylcarbonyl, 4-(1–4C)alkylpiperazin-1-ylcarbonyl, hydroxy-(1–4C)alkyl, (1–4C)alkoxy-(1–4C)alkyl, carboxy(1–4C)alkyl, (1–4C)alkylcarbonyl-(1–4C)alkyl, $CONR^5R^6$(1–4C)alkyl, pyrrolidin-1-ylcarbonyl-(1–4C)alkyl, piperidino-(1–4C)alkyl, morpholino-(1–4C)alkyl, piperazin-1-yl-(1–4C)alkyl and 4-(1–4C)alkylpiperazin-1-yl-(1–4C)alkyl, and wherein any heterocyclic group in said substituent optionally bears 1 or 2 (1–4C)alkyl substituents;

$R^4$ is $CONR^7(CH_2)_nS(O)_pR^8$, $CONH(CH_2)_qNR^9R^{10}$, or the group (1–4C)alkyl-$Y^1$;

wherein n represents an integer 0 to 4;

p represents 0, 1 or 2;

q represents an integer 2 to 4;

$R^7$ represents hydrogen;

$R^8$ represents (1–4C)alkyl, phenyl or (1–4C)alkylphenyl, or $R^7$ and $R^8$ together form a (1–4C)alkylene group;

$R^9$ and $R^{10}$ independently represent hydrogen, (14C) alkyl, phenyl, (1–4C)alkylphenyl, $S(O)_pR^8$, $COR^{11}$ or a 5- or 6-membered monocyclic heteroaryl ring containing up to 3 heteroatoms selected from nitrogen, oxygen and sulphur;

$R^{11}$ represents hydrogen, (1–4C)alkyl, phenyl or (1–4C) alkylphenyl;

$Y^1$ represents $S(O)_pR^8$, $NHS(O)_2R^8$, $NHCOR^{12}$, $O(CH_2)_rR^{13}$, pyrrolidin-1-yl, piperidino, morpholino, thiamorpholino, 1-oxothiamorpholino, 1,1-dioxothiamorpholino or piperazin-1yl, $R^{12}$ represents (1–4C)alkyl, phenyl or (1–4C)alkylphenyl;

r represents an integer 1 to 4;

when r represents an integer 2 to 4, $R^{13}$ represents hydroxy, (1–4C)alkoxy, carboxy, (1–4C) alkoxycarbonyl, $S(O)_pR^8$ or $NR^5R^6$; and when r represents 1, $R^{13}$ represents carboxy or (1–4C) alkoxycarbonyl;

wherein any heterocyclic group within $R^4$ optionally bears 1 or 2 substituents selected from carboxy, CONR$^5$R$^6$, (1–4C)alkyl and (1–4C)alkoxycarbonyl, and any phenyl group within R$^4$ optionally bears 1 or 2 substituents selected from halogeno, trifluoromethyl, cyano, (1–4C)alkyl and (1–4C)alkoxy;

X$^1$ is a group of the formula O, S(O)$_p$, CO, COO, CONR$^{14}$ or CR$^{15}$R$^{16}$;

R$^5$, R$^6$, R$^{14}$, R$^{15}$ and R$^{16}$ independently represent hydrogen or (1–4C)alkyl; and Q represents phenyl, naphthyl, phenyl-(1–4C)alkyl or a heterocyclic moiety containing up to 4 heteroatoms selected from nitrogen, oxygen and sulphur, and Q optionally bears 1, 2 or 3 substituents selected from halogeno, trifluoromethyl, trifluoromethoxy, cyano, hydroxy, NR$^5$R$^6$, nitro, trifluoromethanesulphonyl, carboxy, CONR$^5$R$^6$, (1–4C)alkyl, (1–4C)alkoxy, (1–4C)alkylS(O)$_p$, (1–4C)alkoxycarbonyl, (2–4C)alkanoyl, (2–4C)alkanoylamino, hydroxy-(1–4C)alkyl, (1–4C)alkoxy-(1–4C)alkyl, carboxy-(1–4C)alkyl, (1–4C)alkoxycarbonyl-(1–4C) alkyl, CONR$^5$R$^6$(1–4C)alkyl, phenyl, heteroaryl, phenoxy, phenylS(O)$_p$, benzyl, benzoyl, heteroaryloxy, heteroarylS(O)$_p$, wherein said heteroaryl-containing substituent comprises a 5- or 6-membered monocyclic heteroaryl ring containing up to 3 heteroatoms selected from nitrogen, oxygen and sulphur, and wherein said phenyl, heteroaryl, phenoxy, phenylS(O)$_p$, heteroaryloxy, heteroarylS(O)$_p$, benzyl or benzoyl substituent optionally bears 1, 2 or 3 substituents selected from halogeno, trifluoromethyl, cyano, hydroxy, NR$^5$R$^6$, nitro, carboxy, CONR$^5$R$^6$, (1–4C)alkyl, (1–4C)alkoxy, (1–4C)alkoxycarbonyl and (2–4C)alkanoylamino;

or a phamaceutically-acceptable salt thereof.

In this specification the term "alkyl" includes both straight and branched chain, saturated and unsaturated alkyl groups but references to individual alkyl groups such as "propyl" are specific for the straight chain version only. An analogous convention applies to other generic terms.

It is to be understood that certain aminoheterocyclic derivatives of the present invention can exist in solvated as well as unsolvated forms such as, for example, hydrated forms. It is to be understood that the invention encompasses all such solvated forms which possess Factor Xa inhibitory activity.

It is further to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or by resolution of a racemic form.

Suitable values for the generic terms referred to above include those set out below.

When m is 2, each R$^1$ is independently selected from the list of substituents defined hereinbefore.

A suitable value for R$^1$ when it is a halogeno group or for a halogeno substituent on a phenyl group within the definition of R$^4$, on Q or on a phenyl- or heteroaryl-containing substituent on Q is, for example, fluoro, chloro, bromo or iodo.

A suitable value for R$^1$ when it is a (1–4C)alkyl group or for a (1–4C)alkyl substituent on a heterocyclic or phenyl group within the definition of R$^4$, on Q or on a phenyl- or heteroaryl-containing substituent on Q is, for example, methyl, ethyl, propyl, isopropyl, butyl, isobutyl, sec-butyl or tert-butyl.

A suitable value for R$^1$ when it is a (1–4C)alkoxy group or for a (1–4C)alkoxy substituent on a phenyl group within the definition of R$^4$, on Q or on a phenyl- or heteroaryl-containing substituent on Q is, for example, methoxy, ethoxy, propoxy, isopropoxy or butoxy.

A suitable value for R$^1$ when it is a (1–4C) alkylamino group or for a (1–4C)alkylamino substituent on Q or on a phenyl- or heteroaryl-containing substituent on Q is, for example, methylamino, ethylamino or propylamino.

A suitable value for R$^1$ when it is di-(1–4C)alkylamino or for a di-(1–4C)alkylamino substituent on Q or on a phenyl- or heteroaryl-containing substituent on Q is, for example, dimethylamino, N-ethyl-N-methylamino or diethylamino.

A suitable value for R$^2$, R$^3$, R$^5$, R$^6$ or any one of R$^8$ to R$^{16}$ when it is (1–4C)alkyl is, for example, methyl, ethyl, propyl, isopropyl, butyl or sec-butyl.

A suitable value for a (1–4C)alkylene group formed by R$^2$ and R$^3$ together is, for example, methylene, ethylene, trimethylene or tetramethylene.

A suitable value for L$^1$ when it is (1–4C)alkylene is, for example, methylene, ethylene, trimethylene or tetramethylene; when it is (3–6C)cycloalkane-1,2-diyl is, for example, cyclopropane-1,2-diyl, cyclobutane-1,2-diyl, cyclopentane-1,2-diyl or cyclohexane-1,2-diyl; and when it is (1–3C)alkylene-carbonyl is, for example, methylenecarbonyl, ethylenecarbonyl or trimethylenecarbonyl.

A suitable value for a substituent which may be present on 1 or 2 methylene groups within L$^1$ or the ring formed when R$^2$ and R$^3$ are linked is, for example, as follows:

| | |
|---|---|
| for (1–4C)alkyl: | methyl, ethyl and propyl; |
| for (1–4C)alkoxycarbonyl: | methoxycarbonyl, ethoxycarbonyl, propoxycarbonyl and tert-butoxycarbonyl; |
| for N-(1–4C)alkylcarbamoyl: | N-methylcarbamoyl, N-ethylcarbamoyl and N-propylcarbamoyl; |
| for N,N-di-[(1–4C)alkyl]-carbamoyl: | N,N-dimethylcarbamoyl, N-ethyl-N-methylcarbamoyl and N,N-diethylcarbamoyl; |
| for 4-(1–4C)alkylpiperazin-1-ylcarbonyl: | 4-methylpiperazin-1-ylcarbonyl and 4-ethylpiperazin-1-ylcarbonyl; |
| for hydroxy-(1–4C)alkyl: | hydroxymethyl, 1-hydroxyethyl, 2-hydroxyethyl and 3-hydroxypropyl; |
| for (1–4C)alkoxy-(1–4C)alkyl: | methoxymethyl, ethoxymethyl, 1-methoxymethyl,2-methoxyethyl, 2-ethoxyethyl and 3-methoxypropyl; |
| for carboxy-(1–4C)alkyl: | carboxymethyl, 1-carboxyethyl, 2-carboxyethyl and 3-carboxypropyl; |
| for (1–4C)alkoxycarbonyl-(1–4C)alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |
| for carbamoyl-(1–4C)alkyl: | carbamoylmethyl, 1-carbamoylethyl, 2-carbamoylethyl and 3-carbamoylpropyl; |
| for N-(1–4C)alkylcarbamoyl-(1–4C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di-[(1–4C)alkyl]-carbamoyl-(1–4C)alkyl: | N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, |

| | -continued |
|---|---|
| | 2-(N,N-diethylcarbamoyl)ethyl and 3-(N,N-dimethylcarbamoyl)propyl; |
| for pyrrolidin-1-ylcarbonyl-(1–4C)alkyl: | pyrrolidin-1-ylcarbonylmethyl, 1-(pyrrolidin-1-ylcarbonyl)ethyl and 2-(pyrrolidin-1-ylcarbonyl)ethyl; |
| for piperidinocarbonyl-(1–4C)alkyl: | piperidinocarbonylmethyl, 1-(piperidinocarbonyl)ethyl and 2-(piperidinocarbonyl)ethyl; |
| for morpholinocarbonyl-(1–4C)alkyl: | morpholinocarbonylmethyl, 1-(morpholinocarbonyl)ethyl and 2-(morpholinocarbonyl)ethyl; |
| for piperazin-1-ylcarbonyl-(1–4C)alkyl: | piperazin-1-ylcarbonylmethyl, 1-(piperazin-1-ylcarbonyl)ethyl and 2-(piperazin-1-ylcarbonyl)ethyl; |
| for 4-(1–4C)alkylpiperazin-1-ylcarbonyl-(1–4C)alkyl: | 4-methylpiperazin-1-ylcarbonylmethyl, 4-ethylpiperazin-1-ylcarbonylmethyl, 2-(4-methylpiperazin-1-ylcarbonyl)ethyl and 2-(4-ethylpiperazin-1-ylcarbonyl)ethyl. |

A suitable value for a (1–4C)alkyl group which may be present on a heterocyclic group in a substituent on $L^1$ or the ring formed when $R^2$ and $R^3$ are linked is, for example, methyl, ethyl or propyl.

Suitable values for substituents which may be present on a heterocyclic or phenyl group within the definition of $R^4$, on Q or on a phenyl- or heteroaryl-containing substituent on Q include, for example:

| | |
|---|---|
| for (2–4C)alkenyl: | vinyl and allyl; |
| for (2–4C)alkynyl: | ethynyl and prop-2-ynyl; |
| for (2–4C)alkenyloxy: | vinyloxy and allyloxy; |
| for (2–4C)alkynyloxy: | ethynyloxy and prop-2-ynyloxy; |
| for (1–4C)alkylthio: | methylthio, ethylthio and propylthio; |
| for (1–4C)alkylsulphinyl: | methylsulphinyl, ethylsulphinyl and propylsulphinyl; |
| for (1–4C)alkylsulphonyl: | methylsulphonyl, ethylsulphonyl and propylsulphonyl; |
| for (2–4C)alkanoylamino: | acetamido, propionamido and butyramido; |
| for (1–4C)alkoxycarbonyl: | methoxycarbonyl, ethoxycarbonyl, propoxycarbonyl and tert-butoxycarbonyl; |
| for N-(1–4C)alkylcarbamoyl: | N-methylcarbamoyl, N-ethylcarbamoyl and N-propylcarbamoyl; |
| for N,N-di-[(1–4C)alkyl]-carbamoyl: | N,N-dimethylcarbamoyl, N-ethyl-N-methylcarbamoyl and N,N-diethylcarbamoyl; |
| for (2–4C)alkanoyl: | acetyl, propionyl and butyryl; |
| for hydroxy-(1–4C)alkyl: | hydroxymethyl, 1-hydroxyethyl, 2-hydroxyethyl and 3-hydroxypropyl; |
| for (1–4C)alkoxy-(1–4C)alkyl: | methoxymethyl, ethoxymethyl, 1-methoxyethyl, 2-methoxyethyl, 2-ethoxyethyl and 3-methoxypropyl, |
| for carboxy-(1–4C)alkyl: | carboxymethyl, 1-carboxyethyl, 2-carboxyethyl and 3-carboxypropyl; |
| for (1–4C)alkoxycarbonyl-(1–4C)alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |
| for carbamoyl-(1–4C)alkyl: | carbamoylmethyl, 1-carbamoylethyl, 2-carbamoylethyl and 3-carbamoylpropyl; |
| for N-(1–4C)alkylcarbamoyl-(1–4C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di-[(1–4C)alkyl]-carbamoyl-(1–4C)alkyl: | N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; |

A suitable value for Q when it is naphthyl is, for example, 1-naphthyl or 2-naphthyl; when it is phenyl-(1–4C)alkyl is, for example, benzyl, phenethyl and 3-phenylpropyl, when it is phenyl-(2–4C)alkenyl is, for example, styryl, cinnamyl or 3-phenylprop-2-enyl; and when it is phenyl-(2–4C)alkynyl is, for example, 2-phenylethynyl, 3-phenylprop-2-ynyl and 3-phenylprop-1-ynyl.

A suitable value for Q when it is a heterocyclic moiety containing up to 4 heteroatoms selected from nitrogen, oxygen and sulphur is, for example, a 5- or 6-membered heterocyclic moiety which is a single ring or is fused to one or two benzo rings such as furyl, benzofuranyl, tetrahydrofuryl, chromanyl, thienyl, benzothienyl, pyridyl, piperidinyl, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, quinoxalinyl, quinazolinyl, cinnolinyl, pyrrolyl, pyrrolidinyl, indolyl, indolinyl, imidazolyl, benzimidazolyl, pyrazolyl, indazolyl, oxazolyl, benzoxazolyl, isoxazolyl, thiazolyl, benzothiazolyl, isothiazolyl, morpholinyl, 4H-1,4-benzoxazinyl, 4H-1,4-benzothiazinyl, 1,2,3-triazolyl, 1,2,4-triazolyl, oxadiazolyl, furazanyl, thiadiazolyl, tetrazolyl, dibenzofuranyl and dibenzothienyl, which may be attached through any available position including, for an appropriate $X^1$ group such as, for example, $SO_2$, $CR^{15}R^{16}$ or CO, through any available nitrogen atom and which may bear up to three substituents including a substituent on any available nitrogen atom.

A suitable value for the heteroaryl substituent on Q or the heteroaryl group in a heteroaryl-containing substituent on Q which comprises a 5- or 6-membered monocyclic heteroaryl ring containing up to 3 heteroatoms selected from oxygen, nitrogen and sulphur is, for example, furyl, thienyl, pyridyl, pyrazinyl, pyrimidinyl, pyridazanyl, pyrrolyl, imidazolyl, pyrazolyl, oxazolyl, isoxazolyl, thiazolyl, isothiazolyl, 1,2, 3-triazolyl, 1,2,4-triazolyl, oxadiazolyl, furazanyl and thiadiazolyl which may be attached through any available position including through any available nitrogen atom.

For the avoidance of any doubt it is to be understood that, in the portion of the structure of formula I which has the formula —N(R²)—L¹—T¹(R³)—X¹, it is the N atom which is attached to $L^1$ and it is the $T^1$ group which is attached to the CO i.e. neither of the $R^2$ and $R^3$ groups are attached to $L^1$.

It is further to be understood that, within the structure of formula I, when $R^2$ and $R^3$ together form a methylenecarbonyl group, it is the methylene group thereof which is attached to the N atom and the carbonyl group thereof which is attached to $T^1$. Similarly when $L^1$ is a (1–3C)alkylenecarbonyl group, for example a methylenecarbonyl group, it is the methylene group thereof which is attached to the N atom and the carbonyl group thereof which is attached to $T^1$.

A suitable pharmaceutically-acceptable salt of an aminoheterocyclic derivative of formula I is, for example, an acid-addition salt of an aminoheterocyclic derivative of formula I which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of an aminoheterocyclic derivative of formula I which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention include, for example, aminoheterocyclic derivatives of formula I, or pharmaceutically-acceptable salts thereof, wherein, unless otherwise stated, each of $G^1$, $G^2$, m, $R^1$, $R^2$, $R^3$, $R^4$, $L^1$, $T^1$, $X^1$ and Q has any of the meanings defined hereinbefore or in this section concerning particular compounds of the invention:

(a) each of $G^1$ and $G^2$ is CH;

(b) $G^1$ is CH and $G^2$ is N, or $G^1$ is N and $G_2$ is CH;

(c) m is 0;

(d) $L^1$ is (1–4C)alkylene, $T^1$ is CH or N, and $R^2$ and $R^3$ together form a (1–4C)alkylene group, and wherein 1 or 2 methylene groups within $L^1$ and the ring formed when $R^2$ and $R^3$ are linked optionally bears 1 or 2 (1–4C)alkyl substituents;

(e) $L^1$ is ethylene, $T^1$ is CH, and $R^2$ and $R^3$ together form a methylene or ethylene group;

(f) $L^1$ is ethylene, $T^1$ is CH or N, and $R^2$ and $R^3$ together form an ethylene group;

(g) $L^1$ is ethylene, $T^1$ is CH, and $R^2$ and $R^3$ together form an ethylene group;

(h) $R^4$ is a group of formula $CONR^7(CH_2)_nS(O)_pR^8$ or $CONH(CH_2)_qNR^9R^{10}$;

(i) $X^1$ is a group of the formula $S(O)_p$;

(j) $X^1$ is a group of the formula $SO_2$;

(k) Q is phenyl, naphthyl or phenyl-(1–4C)alkyl which optionally bears 1, 2 or 3 substituents selected from hydroxy, halogeno, cyano, trifluoromethyl, (1–4C)alkyl, (1–4C)alkoxy, phenyl, phenoxy, phenylS(O)$_p$, benzyl and benzoyl, and wherein the phenyl substituent or the phenyl group in a phenyl-containing substituent optionally bears 1 or 2 substituents selected from halogeno, (1–4C)alkyl and (1–4C)alkoxy;

(l) Q is phenyl which bears a phenyl substituent and optionally bears 1 or 2 substituents selected from hydroxy, halogeno, cyano, trifluoromethyl, (1–4C) alkyl and (1–4C)alkoxy, and wherein the phenyl substituent optionally bears up to 3 substituents selected from halogeno, trifluoromethyl, cyano, (1–4C) alkyl and (1–4C)alkoxy;

(m) Q is phenyl-(1–4C) alkyl, phenyl-(2–4C)alkenyl or phenyl-(2–4C)alkynyl which optionally bears 1, 2 or 3 substituents selected from halogeno, cyano, trifluoromethyl, (1–4C)alkyl and (1–4C)alkoxy;

(n) Q is phenyl-(2–4C)alkenyl which optionally bears 1,2 or 3 substituents selected from halogeno, cyano, trifluoromethyl, (1–4C)alkyl and (1–4C)alkoxy;

(o) Q is phenyl or phenyl-(1 –4C)alkyl which bears 1 substituent selected from heteroaryl, heteroaryloxy, heteroarylthio, heteroarylsulphinyl and heteroarylsulphonyl, wherein the heteroaryl substituent or the heteroaryl group in a heteroaryl-containing substituent comprises a 5- or 6-membered monocyclic heteroaryl ring containing up to 3 heteroatoms selected from nitrogen, oxygen and sulphur, and wherein said heteroaryl or heteroaryl-containing substituent optionally bears 1 or 2 substituents selected from halogeno, (1–4C)alkyl and (1–4C)alkoxy;

(p) Q is phenyl which bears 1 substituent selected from heteroaryl, heteroaryloxy, heteroarylthio and heteroarylsulphonyl, wherein the heteroaryl substituent or the heteroaryl group in a heteroaryl-containing substituent is selected from thienyl, pyridyl, pyrimidinyl, pyrazolyl, oxazolyl, thiazolyl, 1,2,3-triazolyl and 1,2, 4-triazolyl, and wherein said heteroaryl or heteroaryl-containing substituent optionally bears 1 or 2 substituents selected from halogeno and (1–4C)alkyl;

(q) Q is naphthyl which optionally bears 1 or 2 substituents selected from hydroxy, halogeno, cyano, trifluoromethyl, (1–4C) alkyl and (1–4C)alkoxy;

(r) Q is a heterocyclic moiety containing up to 2 heteroatoms selected from benzofuranyl, quinolyl, tetrahydroquinolyl, isoquinolyl, quinoxalinyl, quinazolinyl, cinnolinyl, indolyl, benzimidazolyl, indazolyl, benzoxazolyl and benzothiazolyl, and Q optionally bears 1 or 2 substituents selected from halogeno, cyano, trifluoromethyl, (1–4C)alkyl and (1–4C)alkoxy;

(s) Q is a heterocyclic moiety containing up to 2 heteroatoms selected from benzofuranyl, quinolyl, tetrahydroquinolyl, isoquinolyl, quinoxalinyl, quinazolinyl, cinnolinyl, indolyl, benzimidazolyl, indazolyl, benzoxazolyl, benzothiazolyl, dibenzofuranyl and dibenzothienyl, and Q optionally bears 1 or 2 substituents selected from halogeno, cyano, trifluoromethyl, (1–4C) alkyl and (1–4C)alkoxy;

(t) Q is a heterocyclic moiety containing up to 4 heteroatoms selected from furyl, thienyl, pyridyl, pyrimidinyl, pyrrolyl, pyrrolidinyl, imidazolyl, pyrazolyl, oxazolyl, isoxazolyl, thiazolyl, isothiazolyl, 1,2,3-triazolyl, 1,2, 4-triazolyl, oxadiazolyl, thiadiazolyl and tetrazolyl, and Q optionally bears 1 or 2 substituents selected from halogeno, cyano, carboxy, $CONR^5R^6$, (1–4C) alkoxycarbonyl, (1–4C)alkyl, (1–4C)alkoxy;

(u) Q is a heterocyclic moiety containing up to 2 heteroatoms selected from thienyl, pyridyl, pyrimidinyl, imidazolyl, pyrazolyl, oxazolyl and thiazolyl, and Q optionally bears 1 or 2 substituents selected from halogeno, (1–4C)alkyl, (1–4C)alkoxy, phenyl, heteroaryl, phenoxy, phenylthio, phenylsulphinyl, phenylsulphonyl, heteroaryloxy, heteroarylthio, heteroarylsulphinyl, heteroarylsulphonyl, benzyl and benzoyl, wherein the heteroaryl substituent or the heteroaryl group in a heteroaryl-containing substituent is selected from thienyl, pyridyl, pyrimidinyl, pyrazolyl, oxazolyl and thiazolyl, and wherein said phenyl, phenyl-containing, heteroaryl or heteroaryl-containing substituent optionally bears 1 or 2 substituents selected from halogeno, (1–4C)alkyl and (1–4C)alkoxy; or (v) Q is a heterocyclic moiety containing up to 2 heteroatoms selected from thienyl, pyridyl, oxazolyl and thiazolyl, and Q bears a substituent selected from phenyl, thienyl, pyridyl, pyrimidinyl, oxazolyl and thiazolyl, which substituent optionally bears 1 or 2 substituents selected from halogeno, (1–4C)alkyl and (1–4C) alkoxy, and Q optionally bears a further substituent selected from halogeno and (1–4C)alkyl; or a pharmaceutically-acceptable salt thereof.

A preferred compound of the invention is an aminoheterocyclic derivative of formula I, wherein each of $G^1$ and $G^2$ is CH, $G^1$ is CH and $G^2$ is N, or $G^1$ is N and $G^2$ is CH;

m is 0;

$L^1$ is ethylene, $T^1$ is CH or N, and $R^2$ and $R^3$ together form an ethylene group;

$R^4$ is a group of formula $CONR^7(CH_2)_nS(O)_pR^8$ or $CONH(CH_2)_qNR^9R^{10}$;

$X^1$ is a group of the formula $S(O)_p$; and

Q is phenyl, styryl, 4-biphenylyl or 2-naphthyl which optionally bears 1 or 2 substituents selected from fluoro, chloro, bromo, trifluoromethyl, methyl and methoxy; or a pharmaceutically-acceptable salt thereof.

A further preferred compound of the invention is an aminoheterocyclic derivative of formula I, wherein each of $G^1$ and $G^2$ is CH;

m is 0;

$L^1$ is ethylene, $T^1$ is N, and $R^2$ and $R^3$ together form an ethylene group;

$R^4$ is a group of formula $CONR^7(CH_2)_nS(O)_p$ $R^8$ or $CONH(CH_2)_qNR^9R^{10}$;

$X^1$ is a group of the formula $SO_2$; and

Q is 2-naphthyl, styryl or 4-biphenylyl which optionally bears 1 or 2 substituents selected from fluoro, chloro and bromo; or a pharmaceutically-acceptable salt thereof.

Specific preferred compounds of the invention are the following aminoheterocyclic derivatives of formula I:

4-(6-bromonaphth-2-ylsulphonyl)-2-[N-(ethylthioethyl)carbamoyl]-1-[1-(4-pyridyl)piperidin-4-ylcarbonyl]piperazine;

4-(6-bromonaphth-2-ylsulphonyl)-2-thiomorpholinocarbonyl-1-[1-(4-pyridyl)piperidin-4-ylcarbonyl]piperazine;

4-(6-bromonaphth-2-ylsulphonyl)-2-(thiomorpholino-1,1-dioxide)carbonyl-1-[1-(4-pyridyl)piperidin-4-ylcarbonyl]piperazine;

4-(6-bromonaphth-2-ylsulphonyl)-2-(3-tetrahydrothiophene 1,1-dioxide)carbomoyl-1-[1-(4-pyridyl)piperidin-4-ylcarbonyl]piperazine; and 4-(6-bromonaphth-2-ylsulphonyl)-2-[N-(2-dimethylaminoethyl)carbamoyl]-1-[1-(4-pyridyl)piperidin-4-ylcarbonyl]piperazine;

or a pharmaceutically-acceptable salt of any one thereof.

An aminoheterocyclic derivative of formula I, or pharmaceutically-acceptable salt thereof, may be prepared by any process known to be applicable to the preparation of structurally-related compounds. Such procedures are provided as a further feature of the invention and are illustrated by the following representative process in which, unless otherwise stated $G^1$, $G^2$, m, $R^1$, $R^2$, $L^1$, $T^1$, $R^3$, $R^4$, $X^1$ and Q have any of the meanings defined hereinbefore, provided that when there is an amino, alkylamino, hydroxy or carboxy group in $R^1$, $L^1$, $R^2$, $R^3$, $R^4$ or Q then any such group is protected by a conventional protecting group which may be removed when so desired by conventional means.

The compounds required as starting materials for the processes described below may be prepared using standard procedures of organic chemistry. The preparation of such starting materials is illustrated within the accompanying Examples; alternatively analogous procedures to those illustrated may be employed by applying no more than the ordinary skill of an organic chemist:

a) For those compounds in which $R^4$ represents $CONR^7(CH_2)_nS(O)_pR^8$ or $CONH(CH_2)_qNR^9R^{10}$ reaction of a corresponding aminoheterocyclic derivative in which $R^4$ represents —COOH, or a reactive derivative thereof, with a compound of formula IIa or IIb:

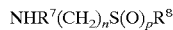   IIa

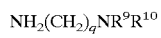   IIb

A suitable reactive derivative of an aminoheterocyclic derivative corresponding to formula I but wherein $R^4$ is —COOH is, for example, an acyl halide, for example an acyl chloride formed by the reaction of the acid and an inorganic acid chloride, for example thionyl chloride; a mixed anhydride, for example an anhydride formed by the reaction of the acid with a chloroformate such as isobutyl chloroformate or with an activated ketone such as 1,1'-carbonyldiimidazole; an active ester, for example an ester formed by the reaction of the acid and a phenol such as pentafluorophenol, an ester such as pentafluorophenyl trifluoroacetate or an alcohol such as N-hydroxybenzotriazole or N-hydroxysuccinimide; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Starting Materials i. The corresponding compounds in which $R^4$ represents COOH may be prepared by the hydrolysis of a corresponding compound in which $R^4$ represents a (1–4C) alkoxycarbonyl group.

The hydrolysis reaction may conveniently be carried out in a conventional manner using, for example, acidic or basic catalysis. A suitable acid for the acidic hydrolysis of an ester group is, for example, an inorganic acid such as hydrochloric or sulphuric acid. A suitable base for the basic hydrolysis of an ester group is, for example, an alkali or alkaline earth metal hydroxide such as sodium hydroxide or potassium hydroxide.

The reaction is conveniently performed in a suitable solvent or diluent such as an alcohol, for example methanol or ethanol, and at a temperature in the range, for example 0° to 120° C., conveniently in the range of 15° to 60° C.

ii. The corresponding compounds of in which $R^4$ represents a (1–4C)alkoxycarbonyl group may be prepared by an analogous process to that described in either process b) or c) below.

Reference may also be made to PCT Application 96/10022 which describes methods for preparing compounds corresponding to formula I, for example wherein $R^4$ is COOH or (1–4C)alkoxycarbonyl.

b) For those compounds in which $T^1$ represents CH, reaction of a corresponding acid of formula III or a reactive derivative thereof, with an amine of formula IV.

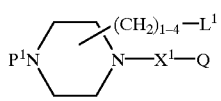

III

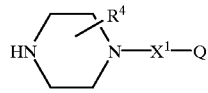

IV

Suitable reactive derivatives of the acid of formula III and reaction conditions etc are as described in a) above.

Starting Materials i. For those compounds of formula IV in which $R^4$ represents (1–4C)alkyl-$Y^1$, and $Y^1$ is other then $O(CH_2)_rR^{13}$, reaction of a compound of formula V, wherein $L^1$ is a leaving group and $P^1$ is a protecting group, with a compound of formula VI, in the presence of a suitable base,

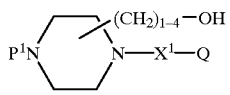

V

VI followed by deprotection.

Suitable groups for $P^1$ are as described in process a). Suitable groups for $L^1$ include chloro, mesylate and tosylate.

ii. For those compounds of formula IV in which $R^4$ represents (1–4C)alkyl-$Y^1$ and $Y^1$ represents $O(CH_2)_rR^{13}$ appropriate manipulation of a compound of formula VII:

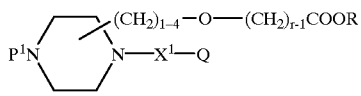

VII iii. Compound of formula VII may be prepared by reaction of a compound of formula VIII, with a compound of formula IX:

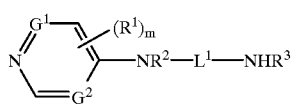

VIII

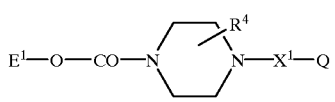

IX wherein $L^2$ represents a leaving group, for example bromo.

c) For those compounds in which $T^1$ represents N, reaction of a corresponding amine of formula X with an ester of formula XI:

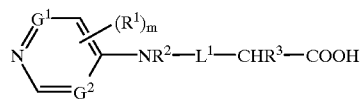

X

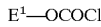

XI

Suitable groups which $E^1$ may represent include 2,4,5-trichlorophenyl and 4-nitrophenyl. The reaction is preferably carried out in a suitable inert solvent or diluent, for example N,N-dimethylformamide, and at a temperature in the range, for example, 50° to 150° C.

Starting Materials i. The esters of formula XI may be prepared by the reaction of a salt, for example the hydrochloride salt, of compound of formula IV with a compound of formula XII:

$E^1$—OCOCl    XII

The reaction is preferably carried out in a suitable inert solvent or diluent, for example methylene chloride, and at a temperature in the range, for example, 0° to 100° C., conveniently at ambient temperature.

d) For the production of those compounds of the formula I wherein $L^1$, $R^2$, $R^3$, $R^4$, or Q bears a $CONR^5R^6$ group, the reaction of a compound of the formula I wherein $L^1$, $R^2$, $R^3$, $R^4$ or Q bears a carboxy group, or a reactive derivative thereof as defined hereinbefore, with ammonia or an appropriate alkylamine or dialkylamine.

The reaction is conveniently performed in a suitable inert solvent or diluent as defined hereinbefore and at a temperature in the range, for example, 0° to 120° C., conveniently in the range 15° to 60°.

e) For the production of those compounds of the formula I wherein $X^1$ is a group of formula SO or $S_2$, wherein $R^4$ contains a SO or $S_2$ group, or wherein Q bears a (1–4C) alkylsulphinyl, (1–4C) alkylsulphonyl, phenylsulphinyl, phenylsulphonyl, heteroarylsulphinyl or heteroarylsulphonyl group, the oxidation of the corresponding compound of the formula I which contains a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15 to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

When a pharmaceutically-acceptable salt of a compound of formula I is required, it may be obtained, for example, by reaction of said compound with a suitable acid or base using a conventional procedure.

When an optically active form of a compound of formula I is required, it may be obtained, for example, by carrying out one of the aforesaid procedures using an optically active starting material or by resolution of a racemic form of said compound using a conventional procedure.

As stated previously, the compounds of formula I are inhibitors of the enzyme Factor Xa. The effects of this inhibition may be demonstrated using one or more of the standard procedures set out hereinafter:

a) Measurement of Factor Xa Inhibition

An in vitro assay system was carried out based on the method of Kettner et al., *J. Biol. Chem.*, 1990, 265, 18289–18297, whereby various concentrations of a test compound were dissolved in a pH7.5 buffer containing 0.5% of a polyethylene glycol (PEG 6000) and incubated at 37° C. with human Factor Xa (0.001 Units/ml, 0.3 ml) for 15 minutes. The chromogenic substrate S-2765 (KabiVitum AB, 20 $\mu$M) was added and the mixture was incubated at 37° C. for 20 minutes whilst the absorbance at 405 nm was measured. The maximum reaction velocity (Vmax) was determined and compared with that of a control sample containing no test compound. Inhibitor potency was expressed as an $IC_{50}$ value.

b) Measurement of Thrombin Inhibition

The procedure of method a) was repeated except that human thrombin (0.005 Units/ml) and the chromogenic substrate S-2238 (KabiVitum AB, 7 $\mu$M) were employed.

c) Measurement of Anticoagulant Activity

An in vitro assay whereby human, rat or rabbit venous blood was collected and added directly to a sodium citrate solution (3.2 g/100 ml, 9 parts blood to 1 part citrate solution). Blood plasma was prepared by centrifugation (1000 g, 15 minutes) and stored at 2–4° C. Conventional prothrombin time (PT) tests were carried out in the presence of various concentrations of a test compound and the concentration of test compound required to double the clotting time, hereinafter referred to as CT2, was determined. In the PT test, the test compound and blood plasma were incubated at 37° C. for 10 minutes. Tissue thromboplastin with calcium (Sigma Limited, Poole, England) was added. Fibrin formation and the time required for a clot to form were determined.

d) An ex vivo Assay of Anticoagulant Activity

The test compound was administered intravenously or orally to a group of Alderley Park Wistar rats. At various times thereafter animals were anaesthetised, blood was collected and PT coagulation assays analogous to those described hereinbefore were conducted. In addition the plasma concentration of compounds is determined by comparison with the anti-Factor Xa activity of a standard compound.

e) An in vivo Measurement of Antithrombotic Activity

Thrombus formation was induced using an analogous method to that described by Vogel et al., *Thromb. Research,* 1989, 54, 399–410. A group of Alderley Park Wistar rats was anaesthetised and surgery was performed to expose the vena cava. Collateral veins were ligated and two loose sutures were located, 0.7 cm apart, round the inferior vena cava. Test compound was administered intravenously or orally. At an appropriate time thereafter tissue thromboplastin (30 $\mu$/kg) was administered via the jugular vein and, after 10 seconds, the two sutures were tightened to induce stasis within the ligated portion of vena cava. After 10 minutes the ligated tissue was excised and the thrombus therein was isolated, blotted and weighed.

f) An in vivo Measurement of Antithrombotic Activity

Using a method similar to that of Smith J R et al Br. J Pharmacol. 1982, 77: 29–38, fasted male Alderley Park rats (360–410 g) are pre-dosed at various times by oral (5 ml/kg) or subcutaneous (1 ml/kg) routes before being anaesthetised with Intraval (120 mg/kg i.p.). The left jugular vein and the right carotid artery are exposed and cannulated with a polypropylene catheters 12 cm in length. An arterio-venous shunt is completed by connecting the two catheters with a 6 cm length of tubing (i.d. 0.3 cm) which contains a 5 cm length of pre-weighed cotton. All tubes were filled with saline prior to the establishment of the circuit. Clamps are removed from the catheters and blood is allowed to flow through the polypropylene tubing for 20 mins. During this time the effect of the test compound on template bleeding time is assessed. The shunt is then closed and the thrombus which has developed on the cotton thread is removed, blotted dry and weighed. Blood samples are also taken at this point by cardiac puncture into 3.2% tri-sodium citrate, plasma is prepared by centrifugation (5 mins 20000 g) and frozen for subsequent prothrombin time and drug level determinations.

The plasma concentration of the compound is extrapolated from the standard curve and expressed in Anti-Factor Xa units. Thrombus weight is measured following dosing of vehicle or test compound. Data is expressed as % inhibition of thrombus formation in the presence of compound when compared to thrombus weight from a group of control animals.

Although the pharmacological potencies of the compounds of formula I vary with structural changes as expected, in general compounds of the formula I possess activity at the following concentrations or doses in at least one of the above tests a) to c):

test a): $IC_{50}$ (Factor Xa) in the range, for example, 0.001–25 $\mu$M;

test b): $IC_{50}$ (thrombin), for example, greater than 10 $\mu$M;

test c): CT2 (PT) in the range, for example, 0.1–50 $\mu$M.

By way of example, the compound of Example 1 as disclosed hereinafter has an $IC_{50}$ of 0.004 $\mu$M against Factor Xa in test a), an $IC_{50}$ of greater than 5 $\mu$M against thrombin in test b) and a CT2(PT) of 1 $\mu$m in test c).

According to a further feature of the invention there is provided a pharmaceutical composition which comprises an aminoheterocyclic derivative of formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an aminoheterocyclic derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an aminoheterocyclic derivative of formula I, or a pharmnaceutically-acceptable salt thereof, for use in a method of treatment of the human or animal body by therapy.

The invention also includes the use of such an active ingredient in the production of a medicament for use in:

(i) producing a Factor Xa inhibitory effect;

(ii) producing an anticoagulant effect;

(iii) producing an antithrombotic effect;

(iv) treating a Factor Xa mediated disease or medical condition;

(v) treating a thrombosis mediated disease or medical condition;

(vi) treating coagulation disorders; and/or (vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of formula I will naturally vary according to the nature and severity of the medical condition, the age and sex of the animal or patient being treated and the route of administration, according to well known principles of medicine. As mentioned above, compounds of the formula I are useful in the treatment or prevention of a variety of medical disorders where anticoagulant therapy is indicated. In using a compound of the formula I for such a purpose, it will generally be administered so that a daily dose in the range, for example, 0.5 to 500 mg/kg body weight is received, given if required in divided doses. In general lower doses will be administered when a parenteral route is employed, for example a dose for intravenous administration in the range, for example, 0.5 to 50 mg/kg body weight will generally be used. For preferred and especially preferred compounds of the invention, in general, lower doses will be employed, for example a daily dose in the range, for example, 0.5 to 10 mg/kg body weight.

Although the compounds of formula I are primarily of value as therapeutic or prophylactic agents for use in warm-blooded animals including man, they are also useful whenever it is required to produce an anticoagulant effect, for example during the ex-vivo storage of whole blood or in the development of biological tests for compounds having anti-coagulant properties.

The compounds of the invention may be administered as a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known anti-hypertensive agent.

The invention will now be illustrated in the following Examples in which, unless otherwise stated:

i. evaporations were carried out by rotary evaporation in vacuo and work-up procedures were carried out after removal of residual solids by filtration;

ii. operations were carried out at room temperature, that is in the range 18–25° C. and under an atmosphere of an inert gas such as argon;

iii. column chromatography (by the flash procedure) and medium pressure liquid chromatography (MPLC) were generally performed on Merck Kieselgel silica (Art. 9385) or Merck Lichroprep RP-18 (Art. 9303) reversed-phase silica obtained from E. Merck, Darmstadt, Germany; alternatively high pressure liquid chromatography (HPLC) was performed on a Dynamax C-18 60 Å preparative reversed-phase column;

iv. yields are given for illustration only and are not necessarily the maximum attainable;

v. the end-products of the formula I have satisfactory microanalyses and their structures were confirmed by nuclear magnetic resonance (NMR) and mass spectral techniques; unless otherwise stated, $CD_3SOCD_3$ solutions of the end-products of the formula I were used for the determination of NMR spectral data, chemical shift values were measured on the delta scale; the following abbreviations have been used: s, singlet; d, doublet; t, triplet; q, quartet; m, multiplet; b, broad;

vi. intermediates were not generally fully characterised and purity was assessed by thin layer chromatographic, infra-red (IR) or NMR analysis;

vii. melting points were determined using a Mettler SP62 automatic melting point apparatus or an oil-bath apparatus; melting points for the end-products of the formula I were generally determined after crystallisation from a conventional organic solvent such as ethanol, methanol, acetone, ether or hexane, alone or in admixture; and viii. the following abbreviations have been used:

| DMF | N,N-dimethylformamide; |
|---|---|
| THF | tetrahydrofuran; |
| DMSO | dimethylsulphoxide. |

EXAMPLE 1

4-(6-Bromonaphth-2-ylsulphonyl)-2-[N-(2-(ethylthio)ethyl)carbamoyl]-[1–1-(4-pyridyl) piperidin-4-ylcarbonyl]piperazine To a suspension of 4-(6-bromonaphth-2-ylsulphonyl)-2-carboxy-1-[1-(4-pyridyl)piperidin-4-ylcarbonyl]piperazine (282 mg) in DMF (4 ml), was added N-(3-dimethylaminopropyl)-N-ethylcarbodiimide (184 mg) and 1-hydroxybenzotriazole (78 mg), followed by a solution of 2-(ethylthio)ethylamine (252 mg) in DMF (1 ml). The resulting mixture was stirred at room temperature for 18 hours. The mixture was partitioned between dichloromethane and water. The organic extracts were dried (MgSO$_4$) and evaporated to a gum, which was purified by chromatography on silica, eluting with increasing polar mixtures of methanol and dichloromethane (up to 13% methanol). There was thus obtained the title compound as a glass (141 mg, 44%).

NMR Spectrum: 1.2 (t, 3H), 1.5–1.8 (m, 4H), 2.4–3.05 (m, 9H), 3.15–3.25 (m, 2H), 3.35–3.5 (m, 1H), 3.6–3.7 (m, 1), 3.75–3.85 (m, 2H), 4.0–4.2 (m, 2H), 4.8–4.9 (m, 1H), 6.75 (d, 2H), 7.5–7.6 (m, 1H), 7.75–7.8 (m, 2H), 8.05–8.15 (m, 4H), 8.3 (d, 1H), 8.4 (d, 1H).

Elemental Analysis: Found C, 48.5; H, 4.85; N, 9.4; $C_{30}H_{36}BrN_5O_4S_2$0.1 $SiO_2$ requires; C, 48.8; H, 5.1; N, 9.4%

The 4-(6-bromonaphth-2-ylsulphonyl)-2-carboxy-1-[1-(4-pyridyl)piperidin-4-ylcarbonyl]piperazine used as starting material was obtained as follows:

Step A

To a solution of ethyl 1-benzyl piperazine-2-carboxylate (E.Jucker, Helv.Chim.Acta (1962), 45, 2383) (6.14 g) in methylene chloride (100 ml) was added triethylamine (10.8 ml) followed by a solution of 6-bromo-2-naphthylsulphonyl chloride (8.4 g) in methylene chloride (50 ml) and the mixture was stirred for 18 hours. The mixture was partitioned between methylene chloride and water. The organic phase was dried (MgSO$_4$) and evaporated. The residue was purified by column chromatography using a 1:4 mixture of ethyl acetate and hexane as eluent. There was thus obtained ethyl 1-benzyl-4-(6-bromo-2-naphthylsulphonyl) piperazine-2-carboxylate as a glassy solid (10.8 g).

NMR Spectrum: 1.2 (t, 3H), 2.4–2.65 (m, 2H), 2.8 (dd, 1H), 3.0–3.1 (m, 1H), 3.5–3.85 (m, 4H), 4.05–4.2 (m, 2H), 7.1–7.3 (m, 5H), 7.75–7.85 (m, 2H), 8.1–8.2 (m, 2H), 8.4 (d, 1H), 8.45 (d, 1H).

Step B

1-Chloroethylchloroformate (5.55 ml) was added to a solution of ethyl 1-benzyl-4-(6-bromo-2-naphthylsulphonyl)piperazine-2-carboxylate (10.5 g) in 1,2-dichloroethane (125 ml) and the mixture was refluxed for 24 hours. The mixture was evaporated and the residue was titurated with hexane. Methanol (100 ml) was added to the resultant gum and the mixture was refluxed for 1.5 hours. The mixture was evaporated and the residue partitioned between methylene chloride and water. The organic phase was dried (MgSO$_4$) and evaporated. The residue was purified by chromatography using increasing polar mixtures of methanol and methylene chloride as eluent. There was thus obtained ethyl-1-(6-bromo-2-naphthylsulphonyl) piperazine-3-carboxylate as a gum (7.95 g).

NMR Spectrum: 1.2 (t, 3H), 2.65–3.1 (m, 6H), 3.3–3.4 (m, 1H), 3.45–3.55 (m, 1H), 4.1 (q, 1H), 7.8–7.85 (m, 2H), 8.1–8.25 (m, 2H), 8.4 (d,1H).

Step C

To a solution of ethyl-1-(6-bromo-2-naphthylsulphonyl) piperazine-3-carboxylate (7.94 g) in methylene chloride (80 ml), cooled to 5° C. was added sodium hydrogen carbonate (15.6 g) followed by a solution of 1-(4-pyridyl)piperidine4-carbonyl chloride (4.6 g) in methylene chloride (20 ml). The resulting mixture was stirred at room temperature for 18 hours. The mixture was partitioned between methylene chloride and water. The organic extracts were dried (MgSO$_4$) and evaporated. The residue was purified by chromatography using increasing polar mixtures of methanol and methylene chloride as eluent. There was thus obtained 2-ethoxycarbonyl4-(6-bromo-2-naphthylsulphonyl)-1-[1-(4-pyridyl)piperidin-4-ylcarbonyl] piperazine as a glass (5.48 g).

NMR Spectrum: 1.2 (t, 3H), 1.5–1.8 (m, 4H), 2.45–2.6 (m, 1H), 2.7–3.05 (m, 5H), 3.65–3.85 (m, 3H), 4.05–4.25 (m, 4H), 5.05–5.1 (m, 1H), 6.7 (d, 2H), 7.75–7.8 (m, 2H), 8.05–8.15 (m, 4H), 8.3 (d, 1H), 8.45(d, 1H).

Elemental Analysis: Found: C, 54.2;H, 5.2;N, 9.0; $C_{28}$, $H_{31}$, $BrN_4O_5S$ requires: C, 54.6; H, 5.1; N, 9.1%

Step D

To a solution of 2-ethoxycarbonyl-4-(6-bromo-2-naphthylsulphonyl)-1-[1-(4-pyridyl)piperidin-4-ylcarbonyl] piperazine(3.30 g) in methanol (60 ml) was added 2N NaOH (10.7 ml). The mixture was warmed to 35° C. and stirred for 30 minutes. The mixture was evaporated to dryness. The resulting solid was dissolved in water and acidified with acetic acid. The precipitate was filtered and washed with water. There was thus obtained 2-carboxy-4-(6-bromo-2-naphthylsulphonyl)-1-[1-(4-pyridyl)piperidin-4-ylcarbonyl] piperazine (2.92 g) m.p. 216–222° C. (dec).

NMR Spectrum: 1.5–1.8 (m, 4H), 2.45–2.55 (m, 1H), 2.7 (dd, 1H), 2.8–3.05 (m, 3H), 3.15–3.35 (bm, 1H), 3.6–4.25 (m, 5H), 4.95–5.0 (m, 1H), 6.7 (d, 2H), 7.7–7.8 (m, 2H), 8.05–8.15 (m, 4H), 8.3 (d, 1H), 8.4 (d, 1H).

Elemental Analysis: Found: C, 52.4;H, 4.8;N, 9.3; $C_{26}H_{27}BrN_4O_5S.0.5H_2O$ requires C, 52.35; H, 4.7; N, 9.4%

EXAMPLE 2

4-(6-Bromonaphth-2-ylsulphonyl)-2-thiomorpholinocarbonyl-1[-1-(4-pyridyl)piperidin-4-ylcarbonyl]piperazine The procedure of Example 1 was repeated using thiomorpholine to give the title compound as a glass (59%), m.p. 250–258° C.;

NMR Spectrum: 1.5–1.8 (m, 4H), 2.55–2.6 (m, 4H), 2.7–3.05 (m, 5H), 3.6–3.85 (m, 9H), 3.95–4.05 (m, 1H), 5.2–5.25 (m, 1H), 6.7 (d, 2H), 7.75–7.85 (m, 2H), 8.1–8.15 (m, 4H), 8.3 (d, 1H), 8.45 (d, 1H).

Elemental Analysis: Found C, 52.6; H, 4.9; N, 10.4; $C_{30}H_{34}BrN_5O_4S_2 \cdot 0.5H_2O$ requires C, 52.8; H, 5.1; N, 10.3%

EXAMPLE 3

4-(6-Bromonaphth-2-ylsulphony)-2-(thiomorpholino-1,1-dioxide)carbonyl-1-[1-(4-pyridyl)piperidin-4-ylcarbonyl]piperazine The procedure of Example 1 was repeated using thiomorpholine-1,1-dioxide to give the title compound as a glass (54%).

NMR Spectrum: 1.5–1.8 (m, 4H), 2.8–3.1 (m, 9H), 3.55–4.0 (m, 10H), 5.2–5.25 (m, 1H), 6.7–6.75 (m, 2H), 7.75–7.85 (m, 2H), 8.05–8.15 (m, 4H), 8.3 (d, 1H), 8.45(d, 1H).

Elemental Analysis: Found C, 49.9; H, 4.9; N, 9.7; S, 8.4; $C_{30}H_{34}BrN_5O_6S_2 \cdot H_2O$ requires: C, 49.9; H, 5.0; N, 9.7; S, 8.9%.

EXAMPLE 4

4-(6-Bromonaphth-2-ylsulphonyl)-2-(3-tetrahydrothiophene-1,1-dioxide)carbamoyl-1-[1-(4-pyridyl)piperidin-4-ylcarbonyl]piperazine The procedure of Example 1 was repeated using 3-amino-tetrahydrothiophene-1,1-dioxide to give the title compound as a glass (79%)

NMR Spectrum: 1.5–1.8 (m, 4H), 2.0–2.15 (m, 1H), 2.25–2.45 (m, 1H), 2.6–3.35 (m, 9H), 3.4–3.55 (m, 1H), 3.6–3.7 (m, 1H), 3.75–3.9 (m, 2H), 4.0–4.15 (m, 2H), 4.35–4.5 (m, 1H), 4,8–4.9 (m, 1H), 6.75 (d, 2H), 7.7–7.8 (m, 2H), 7.95 (d, 1H), 8.05–8.15 (m, 4H), 8.3 (d, 1H), 8.4 (d, 1H).

Elemental Analysis: Found C, 49.1; H, 4.9; N, 9.5, S, 8.9; $C_{30}H_{34}BrN_5O_6S_2 \cdot 1.5H_2O$ requires C, 49.25; H, 5.05; N, 9.6; S, 8.8%

EXAMPLE 5

4-(6-Bromonaphth-2-ylsulphonyl)-2-[N-(2-dimethylaminoethyl)carbamoyl]-1-[1-(4-pyridyl)piperidin-4-ylcarbonyl]piperazine The procedure of Example 1 was repeated using 2-dimethylaminoethylamine to give the title compound as a glass (30%).

NMR Spectrum: ($CD_3SOCD_3$ and $CD_3COOD$) 1.6–1.8 (m, 4H), 2.8 (s, 6H), 3.0–3.2 (m, 4H), 3.25–3.75 (m, 8H), 3.95–4.1 (m, 3H), 4.2–4.3 (m, 1H), 4.95–5.0 (m, 1H), 7.0 (d, 2H), 7.7–7.8 (m, 2H), 8.0–8.1 (m, 4H), 8.25 (d, 1H), 8.4 (d, 1H).

Elemental Analysis: Found: C, 53.8; H, 5.6; N, 12.1; $C_{30}H_{37}BrN_6O_4S \cdot 0.75H_2O$ requires C, 53.7; H, 5.75; N, 12.5%

EXAMPLE 6

The following illustrate representative pharmaceutical dosage forms containing the compound of formula I, or a pharmaceutically-acceptable salt thereof (hereafter compound X), for therapeutic or prophylactic use in humans:

| (a) Tablet 1 | mg/tablet |
|---|---|
| Compound X | 100 |
| Lactose Ph.Eur. | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur. | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur. | 488.5 |
| Magnesium stearate | 1.5 |

| (e) Injection I | (50 mg/ml) |
|---|---|
| Compound X | 5.0% w/v |
| 1M Sodium hydroxide solution | 15.0% w/v |
| 0.1M Hydrochloric acid (to adjust pH to 7.6) | |
| Polyethylene glycol 400 | 4.5% w/v |
| Water for injection to 100% | |

| (f) Injection II | 10 mg/ml) |
|---|---|
| Compound X | 1.0% w/v |
| Sodium phosphate BP | 3.6% w/v |
| 0.1M Sodium hydroxide solution | 15.0% w/v |
| Water for injection to 100% | |

| (g) Injection III | (1 mg/ml,buffered to pH6) |
|---|---|
| Compound X | 0.1% w/v |
| Sodium phosphate BP | 2.26%w/v |
| Citric acid | 0.38%w/v |
| Polyethylene glycol 400 | 3.5% w/v |
| Water for injection to 100% | |

Note
The above formulations may be obtained by conventional procedures well known in the pharmaceutical art. The tablets (a)–(c) may be enteric coated by conventional means, for example to provide a coating of cellulose acetate phthalate.

I claim:
1. A compound of the formula I:

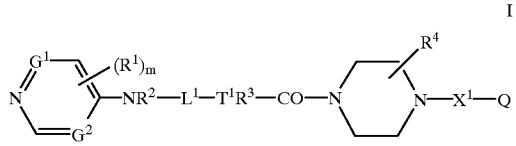

wherein $G^1$ and $G^2$ independently represent CH or N;
m is 0, 1 or 2;

$R^1$ is halogeno, trifluoromethyl, trifluoromethoxy, cyano, $NR^5R^6$, hydroxy, nitro, (1–4C)alkyl or (1–4C)alkoxy;

$T^1$ is CH or N;

$L^1$ is (1–4C)alkylene, (3–6C)cycloalkane-1,2-diyl or (1–3C)alkylene-carbonyl;

$R^2$ is hydrogen or (1–4C)alkyl and $R^3$ is hydrogen or (1–4C)alkyl, or $R^2$ and $R^3$ together form a (1–4C) alkylene or methylenecarbonyl group, wherein 1 or 2 methylene groups within $L^1$ or the ring formed when $R^2$ and $R^3$ are linked optionally bears 1 or 2 substituents selected from carboxy, $CONR^5R^6$, (1–4C)alkyl, (1–4C)alkoxycarbonyl, pyrrolidin-1-ylcarbonyl, piperidinocarbonyl, morpholinocarbonyl, piperazin-1-yl, carbonyl, 4-(1–4C)alkylpiperazin-1-ylcarbonyl, hydroxy-(1–4C)alkyl, (1–4C)alkoxy-(1–4C)alkyl, carboxy-(1–4C)alkyl, (1–4C)alkoxycarbonyl-(1–4C)alkyl, $CONR^5R^6$(1–4C)alkyl, pyrrolidin-1-ylcarbonyl-(1–4C)alkyl, piperidino-(1–4C)alkyl, morpholino-(1–4C)alkyl, piperazin-1-yl-(1–4C)alkyl and 4-(1–4C)alkylpiperazin-1-yl-(1–4C) alkyl, and wherein any heterocyclic group in said substituent optionally bears 1 or 2 (1–4C)alkyl substituents;

$R^4$ is $CONR^7(CH_2)_nS(O)_pR^8$, $CONH(CH_2)_qNR^9R^{10}$, or the group (1–4C)alkyl-$Y^1$;

wherein n represents an integer 0 to 4;

p represents 0, 1 or 2;

q represents an integer 2 to 4;

$R^7$ represents hydrogen;

$R^8$ represents (1–4C)alkyl, phenyl or (1–4C) alkylphenyl, or $R^7$ and $R^8$ together form a (1–4C)alkylene group;

$R^9$ and $R^{10}$ independently represent hydrogen, (1–4C) alkyl, phenyl, (1–4C)alkylphenyl, $S(O)_pR^8$, $COR^{11}$ or a 5- or 6-membered monocyclic heteroaryl ring having up to 3 heteroatoms selected from nitrogen, oxygen and sulphur;

$R^{11}$ represents hydrogen, (1–4C)alkyl, phenyl or (1–4C) alkylphenyl;

$Y^1$ represents $S(O)_pR^8$, $NHS(O)_2R^8$, $NHCOR^{12}$, $O(CH_2)_rR^3$, pyrrolidin-1-yl, piperidino, morpholino, thiamorpholino, 1-oxothiamorpholino, 1,1-dioxothiamorpholino or piperazin-1-yl, $R^{12}$ represents (1–4C)alkyl, phenyl or (1–4C)alkylphenyl;

r represents an integer 1 to 4;

when r represents an integer 2 to 4, $R^{13}$ represents hydroxy, (1–4C)alkoxy, carboxy, (1–4C) alkoxycarbonyl, $S(O)_pR^8$ or $NR^5R^6$; and when r represents 1, $R^{13}$ represents carboxy or (1–4C) alkoxycarbonyl;

wherein any heterocyclic group within $R^4$ optionally bears 1 or 2 substituents selected from carboxy, $CONR^5R^6$, (1–4C)alkyl and (1–4C) alkoxycarbonyl, and any phenyl group within $R^4$ optionally bears 1 or 2 substituents selected from halogeno, trifluoromethyl, cyano, (1–4C) alkyl and (1–4C)alkoxy;

$X^1$ is a group of the formula O, $S(O)_p$, CO, COO, $CONR^{14}$ or $CR^{15}R^{16}$;

$R^5$, $R^6$, $R^{14}$, $R^{15}$ and $R^{16}$ independently represent hydrogen or (1–4C)alkyl; and Q represents phenyl, naphthyl, phenyl-(1–4C)alkyl or a heterocyclic moiety having up to 4 heteroatoms selected from nitrogen, oxygen and sulphur, and Q optionally bears 1, 2 or 3 substituents selected from halogeno, trifluoromethyl, trifluoromethoxy, cyano, hydroxy, $NR^5R^6$, nitro, trifluoromethanesulphonyl, carboxy, $CONR^5R^6$, (1–4C)alkyl, (1–4C)alkoxy, (1–4C)alkylS(O)$_p$, (1–4C)alkoxycarbonyl, (2–4C) alkanoyl, (2–4C)alkanoylamino, hydroxy-(1–4C)alkyl, (1–4C)alkoxy-(1–C)alkyl, carboxy-(1–4C)alkyl, (1–4C)alkoxycarbonyl-(1–4C) alkyl, $CONR^5R^6$(1–4C) alkyl, phenyl, heteroaryl, phenoxy, phenylS(O)$_p$, benzyl, benzoyl, heteroaryloxy, heteroarylS(O)$_p$, wherein said heteroaryl substituent has a 5- or 6-membered monocyclic heteroaryl ring having up to 3 heteroatoms selected from nitrogen, oxygen and sulphur, and wherein said phenyl, heteroaryl, phenoxy, phenylS(O)$_p$, heteroaryloxy, heteroarylS(O)$_p$, benzyl or benzoyl substituent optionally bears 1, 2 or 3 substituents selected from halogeno, trifluoromethyl, cyano, hydroxy, $NR^5R^6$, nitro, carboxy, $CONR^5R^6$, (1–4C) alkyl, (1–4C)alkoxy, (1–4C)alkoxycarbonyl and (2–4C)alkanoylamino;

or a pharmaceutically-acceptable salt thereof.

2. A compound according to claim 1 wherein:

each of $G^1$ and $G^2$ is CH; or $G^1$ is CH and $G^2$ is N, or $G^1$ is N and $G^2$ is CH;

m is 0;

$L^1$ is (1–4C)alkylene, $T^1$ is CH or N, and $R^2$ and $R^3$ together form a (1–4C)alkylene group, and wherein 1 or 2 methylene groups within $L^1$ and the ring formed when $R^2$ and $R^3$ are linked optionally bears 1 or 2 (1–4C)alkyl substituents;

$R^4$ is a group of formula $CONR^7(CH_2)_nS(O)_pR^8$ or $CONH(CH_2)_qNR^9R^{10}$;

$X^1$ is a group of the formula $S(O)_p$;

Q is phenyl, naphthyl or phenyl-(1–4C)alkyl which optionally bears 1, 2 or 3 substituents selected from hydroxy, halogeno, cyano, trifluoromethyl, (1–4C) alkyl, (1–4C)alkoxy, phenyl, phenoxy, phenylS(O)$_p$, benzyl and benzoyl, and wherein the phenyl substituent or the phenyl group in a phenyl-containing substituent optionally bears 1 or 2 substituents selected from halogeno, (1–4C)alkyl and (1–4C)alkoxy; or Q is phenyl-(2–4C)alkenyl or phenyl-(2–4C)alkynyl which optionally bears 1, 2 or 3 substituents selected from halogeno, cyano, trifluoromethyl, (1–4C)alkyl and (1–4C)alkoxy; or Q is phenyl or phenyl-(1–4C)alkyl which bears 1 substituent selected from heteroaryl, heteroaryloxy, heteroarylthio, heteroarylsulphinyl and heteroarylsulphonyl, wherein the heteroaryl substituent or the heteroaryl group in a heteroaryl substituent has a 5- or 6-membered monocyclic heteroaryl ring having up to 3 heteroatoms selected from nitrogen, oxygen and sulphur, and wherein said heteroaryl or heteroaryl substituent optionally bears 1 or 2 substituents selected from halogeno, (1–4C)alkyl and (1–4C)alkoxy; or Q is a heterocyclic moiety having up to 2 heteroatoms selected from benzofuranyl, quinolyl, tetrahydroquinolyl, isoquinolyl, quinoxalinyl, quinazolinyl, cinnolinyl, indolyl, benzimidazolyl, indazolyl, benzoxazolyl, benzothiazolyl, dibenzofuranyl and dibenzothienyl, and Q optionally bears 1 or 2 substituents selected from halogeno, cyano, trifluoromethyl, (1–4C)alkyl and (1–4C)alkoxy; or Q is a heterocyclic moiety having up to 4 heteroatoms selected from furyl, thienyl, pyridyl, pyrimidinyl, pyrrolyl, pyrrolidinyl, imidazolyl, pyrazolyl, oxazolyl, isoxazolyl, thiazolyl, isothiazolyl, 1,2,3-triazolyl, 1,2,4-triazolyl, oxadiazolyl, thiadiazolyl and tetrazolyl, and Q optionally bears 1 or 2 substituents selected from halogeno, cyano, carboxy, $CONR^5R^6$, (1–4C) alkoxycarbonyl, (1–4C)alkyl, (1–4C)alkoxy; or Q is a heterocyclic moiety having up to 2 heteroatoms selected from thienyl, pyridyl, pyrimidinyl, imidazolyl, pyrazolyl, oxazolyl and thiazolyl, and Q optionally bears 1 or 2 substituents selected from halogeno, (1–4C)alkyl, (1–4C)alkoxy, phenyl, heteroaryl, phenoxy, phenylthio, phenylsulphinyl, phenylsulphonyl, heteroaryloxy, heteroarylthio, heteroarylsulphinyl, heteroarylsulphonyl, benzyl and benzoyl, wherein the heteroaryl substituent or the heteroaryl group in a heteroaryl substituent is selected from thienyl, pyridyl, pyrimidinyl, pyrazolyl, oxazolyl and thiazolyl, and wherein said phenyl, phenyl substituent, heteroaryl or heteroaryl substituent optionally bears 1 or 2 substituents selected from halogeno, (1–4C)alkyl and (1–4C)alkoxy;

or a pharmaceutically-acceptable salt thereof.

3. A compound according to claim 1 wherein each of $G^1$ and $G^2$ is CH, $G^1$ is CH and $G^2$ is N, or $G^1$ is N and $G^2$ is CH;

m is 0;

$L^1$ is ethylene, $T^1$ is CH or N, and $R^2$ and $R^3$ together form an ethylene group;

$R^4$ is a group of formula $CONR^7(CH_2)_nS(O)_pR^8$ or $CONH(CH_2)_qNR^9R^{10}$;

$X^1$ is a group of the formula $S(O)_p$; and

Q is phenyl, styryl, 4-biphenylyl or 2-naphthyl which optionally bears 1 or 2 substituents selected from fluoro, chloro, bromo, trifluoromethyl, methyl and methoxy;

or a pharmaceutically-acceptable salt thereof.

4. A compound according to claim 1 wherein each of $G^1$ and $G^2$ is CH;

m is 0;

$L^1$ is ethylene, $T^1$ is N, and $R^2$ and $R^3$ together form an ethylene group;

$R^4$ is a group of formula $CONR^7(CH_2)_nS(O)_pR^8$ or $CONH(CH_2)_qNR^9R^{10}$;

$X^1$ is a group of the formula $SO_2$; and

Q is 2-naphthyl, styryl or 4-biphenylyl which optionally bears 1 or 2 substituents selected from fluoro, chloro and bromo;

or a pharmaceutically-acceptable salt thereof.

5. A compound according to claim 1 which is:

4-(6-bromonaphth-2-ylsulphonyl)-2-[N-(ethylthioethyl)carbamoyl]-1-[1-(4-pyridyl)piperidin-4-ylcarbonyl]piperazine;

4-(6-bromonaphth-2-ylsulphonyl)-2-thiomorpholinocarbonyl-1-[1-(4-pyridyl)piperidin-4-ylcarbonyl]piperazine;

4-(6-bromonaphth-2-ylsulphonyl)-2-(thiomorpholino-1,1-dioxide)carbonyl-1-[1-(4-pyridyl)piperidin-4-ylcarbonyl]piperazine;

4-(6-bromonaphth-2-ylsulphonyl)-2-(3-tetrahydrothiophene 1,1-dioxide)carbomoyl-1-[1-(4-pyridyl)piperidin-4-ylcarbonyl]piperazine; and 4-(6-bromonaphth-2-ylsulphonyl)-2-[N-(2-dimethylaminoethyl)carbamoyl]-1-[1-(4-pyridyl)piperidin-4-ylcarbonyl]piperazine;

or a pharmaceutically-acceptable salt of any one thereof.

6. A pharmaceutical composition which comprises a compound of the formula I or a pharmaceutically acceptable salt thereof as claimed in any one of claims 1 to 5 and a pharmaceutically acceptable carrier.

7. A method for treating coronary artery or cerebrovascular disease comprising the step of administering a compound of the formula I, or a pharmaceutically acceptable salt thereof, as claimed in any one of claims 1 to 5.

8. A process for the preparation of a compound of the formula I or a pharmaceutically acceptable salt thereof as claimed in claim 1, which comprises:

a) for a preparation of those compounds in which $R^4$ represents $CONR^7(CH_2)nS(O)pR^8$ or $CONH(CH_2)qNR^9R^{10}$, reaction of a corresponding compound in which $R^4$ represents COOH, or a reactive derivative thereof, with a compound of the formula IIa or IIb:

b) for the preparation of those compounds in which $T^1$ represents CH, reaction of a corresponding acid of the formula III or a reactive derivative thereof with an amine of the formula IV:

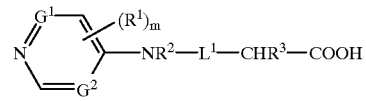

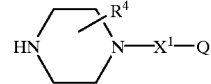

c) for the preparation of those compounds in which $T^1$ represents N, reaction of a corresponding amine of the formula X with an ester of the formula XI:

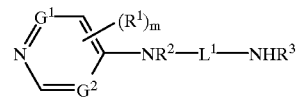

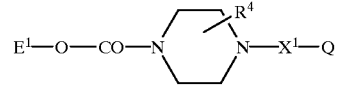

d) for the production of those compounds of the formula I wherein $L^1$, $R^2$, $R^3$, $R^4$ or Q bears a $CONR^5R^6$ group, the reaction of a compound of the formula I wherein $L^1$, $R^2$, $R^3$, $R^4$ or Q bears a carboxy group, or a reactive derivative thereof, with $NHR^5R^6$; or e) for the production of those compounds of the formula I wherein $X^1$ is a group of the formula SO or $SO_2$, wherein $R^4$ has a SO or $SO_2$ group wherein Q bears a (1–4C)alkylsulphinyl, (1–4C)alkysulphonyl, phenylsulphonyl, phenylsulphinyl, heteroarylsulphinyl or heteroarylsulphonyl group, the oxidation of the corresponding compound of the formula I which has a thio group; and if necessary forming a pharmaceutically acceptable salt.

9. A method for producing an antithrombotic or anticoagulant effect in blood comprising the step of administering a compound of the formula I, or a pharmaceutically acceptable salt thereof, as claimed in claim 1.

* * * * *